United States Patent [19]

Piasio

[11] Patent Number: 5,434,053
[45] Date of Patent: Jul. 18, 1995

[54] DETECTION OF ANTIBIOTICS

[75] Inventor: Roger Piasio, South Portland, Me.

[73] Assignee: Gist-Brocades N.V., Netherlands

[21] Appl. No.: 132,469

[22] Filed: Oct. 6, 1993

Related U.S. Application Data

[63] Continuation-in-part of Ser. No. 6,755, Jan. 21, 1993, abandoned.

[30] Foreign Application Priority Data

Oct. 6, 1992 [EP] European Pat. Off. ............ 92203084

[51] Int. Cl.$^6$ ............................................. G01N 33/543
[52] U.S. Cl. ...................................... 435/79; 435/7.92; 435/7.93; 435/28; 436/518; 436/815
[58] Field of Search ..................... 435/7.9, 7.92, 7.93, 435/28, 810, 971, 973; 436/501-518, 528, 808, 815, 822; 530/391.5, 391.7, 391.9, 807

[56] References Cited

U.S. PATENT DOCUMENTS 4,239,852 12/1980 Charm .................................. 435/32

OTHER PUBLICATIONS

Kachab et al J. Imm. Mem. 147 pp. 33–41 (1992).
Campbell et al. Antimicrobial Agents–Chemotherapy 25 #2 pp. 205–211 (1984).

*Primary Examiner*—Toni R. Scheiner
*Assistant Examiner*—Lora M. Green
*Attorney, Agent, or Firm*—Bierman and Muserlian

[57] ABSTRACT

A process for the detection of antibiotics in a liquid medium such as milk, urine and blood is disclosed which comprises bringing together a fluid sample of the liquid medium, an labelled antibiotic binding protein, and an immobilized antibiotic, allowing the labelled antibiotic binding protein to bind with the immobilized antibiotic, removing labelled antibiotic binding protein which is not bound to immobilized antibiotic, and determining the amount of the labelled antibiotic binding protein bound to the immobilized antibiotic.

11 Claims, No Drawings

DETECTION OF ANTIBIOTICS

PRIOR APPLICATION

The present application is a continuation in part of U.S. patent application Ser. No. 006,755, filed Jan. 21, 1993, now abandoned.

The present process relates to the detection of antibiotics in a liquid medium such as milk, urine and blood.

In U.S. Pat. No. 4,239,852 and U.S. Pat. No. 4,239,745 a process of detecting the presence of an antibiotic in a liquid sample is disclosed in which the sample is incubated with cell parts of a microorganism. Any antibiotic molecules in the liquid sample bind to the receptor sites of the cell parts. After this incubation step a tagged antibiotic is added which is then allowed to bind to the remaining receptor sites. After the liquid has been separated from the cell parts and washed, the amount of tagged antibiotic bound to receptor sites can be determined. In the examples of these patents, radioactively tagged antibiotics are used. Also the commercially available tests, developed on the disclosure of the patents, are available which utilize the competition between radioactive labelled antibiotic and sample antibiotic. Although this technique is very sensitive, it requires trained personnel and expensive equipment. Another disadvantage is the usual radiation hazard. Therefore there has not been available a fast, acceptable test for antibiotics which can be used routinely, particularly by farm and dairy plant workers.

In the above U.S. patents, a test based on the competition of an enzyme tagged antibiotic and a sample antibiotic is also mentioned. In example 2 of U.S. Pat. No. 4,239,852 a test kit is described which is able to detect 0.05 units of penicillin per milliliter (=30 ppb) within a minimum of 20 minutes. The detection of smaller concentrations of penicillin requires longer test times.

Since the concentrations of antibiotics present in milk are generally very low, time constraint mean that a detection method based on enzyme tagged antibiotics is not convenient for testing milk samples daily.

It is therefore an object of the present invention to provide a simple test designed to detect low levels of antibiotics in liquid media such as milk, urine or blood. The time required for the tests should ideally not exceed about 15 minutes. The present invention provides a process for the detection of at least one antibiotic in a liquid medium such as milk, urine and blood which comprises (a) bringing together a fluid sample of the liquid medium, at least one labelled antibiotic binding protein, and at least one immobilized antibiotic.
(b) allowing the labelled antibiotic binding protein to bind with the immobilized antibiotic,
(c) removing labelled antibiotic binding protein which is not bound to immobilized antibiotic, and
(d) determining the amount of the labelled antibiotic binding protein bound to the immobilized antibiotic.

The process may be used to detect a wide variety of antibiotics such as β-lactams (including penicillins such as benzylpenicillin, and cephalosporins), tetracyclines, gentamycine, sulpha compounds such as sulpha methazine, and combinations thereof. The immobilized antibiotic is generally the same as that present in the liquid sample, but may be different. For example the immobilized antibiotic may be an analogue of the antibiotic in the sample. If the immobilized antibiotic and the antibiotic are different they should both be able to bind with the binding protein.

The label used in the present invention may be an enzyme or a fluorescent compound such as FITC (fluorescein isothiocyanate) or TRITC (tetramethyl rhodamine isothiocyanate). Preferably an enzyme-labelled antibiotic protein is used in step (a).

According to one embodiment of the invention an assay can be used to detect a combination of different antibiotics within one test. In such a test different labelled antibiotic binding proteins in combination with the several antibiotics immobilised are present.

Surprisingly it has been found that by labelling the antibiotic binding protein with an enzyme, and immobilizing the antibiotic of interest on a solid phase such as a test tube or dipstick, a test kit is obtained which is sensitive to at least 5 ppb benzylpenicillin (1 mg corresponds to 1592 i.u. benzyl penicillin-K-salt). Moreover the time required for such a test does not exceed about 12 minutes. The test is inexpensive and easy to perform and does not require trained personnel. Smaller concentrations may be detected if the incubation time is extended.

According to a preferred embodiment of the invention step (a) comprises bringing the labelled antibiotic binding protein into contact with the liquid sample, allowing the antibiotic in the sample to bind to the labelled antibiotic binding protein, and subsequently adding immobilized antibiotic. The binding protein and liquid sample are generally incubated for 1 to 4 minutes, prior to the addition of the immobilized antibiotic.

The labelled antibiotic binding protein comprises any antibiotic binding protein for example those which may be obtained from an antibiotic-sensitive microorganism, such as a *Bacillus stearothermophilus, Bacillus subtilis, Streptococcus thermophilus* or *Escherichia coli*, preferably *Bacillus stearothermophilus* microorganism is used. Also antibiotic binding proteins such as antibodies are embodied in the present invention. Suitable antibodies can be obtained by immunisation of animals, see for example E. H. Kachab et al, The Journal of Immunological Methods, vol. 147, no. 1, Jan. 1, 1992, page 33–41. The antibiotic-binding protein may be purified by techniques as affinity chromatography or gel filtration.

The labelled antibiotic binding protein has a reactive site for binding to the antibiotics of the sample as well as to the immobilized antibiotics. The antibiotic binding protein is linked to the label. All methods available that are known to generate a protein/protein interaction could be suitably used to obtain the above mentioned complex. For instance, linkage could be realized by means of bifunctional reagents. Besides a covalent interaction, binding between different proteins could also be based on local charge differences on adjacent surfaces (Van der Waals forces) and/or hydrophobic binding (G. E. Davies and G. R. Stark (1970): Use of dimethyl suberimidate, a cross-linking reagent, in studying the subunit structure of oligomeric proteins. Proc. Natl. Acad. Sci. USA, 66: 651–656; F. Wold (1972): Bifunctional reagents: Methods Enzymol. 25: 623–651; J. R. Knowles (1972): Photogenerated labels for biological receptor-site labelling: Acc. Chem. Res. 5: 155–160; K. Peters and F. M. Richards (1977): Chemical cross-linking: reagents and problems in studies of membrane structure: Ann. Rev. Biochem. 46: 523–551; W. S. Jacoby and M. Wilchek (eds.): Affinity labelling: Methods Enzymol. 46; M. Das and C. F. Fox (1979) Chemical cross-linking in biology: Ann. Rev. Biophys. Bioeng. 8: 165–193; M. R. Bosshard (1979): Mapping of contact areas in protein-nucleic acid and protein-protein complexes by differential chemical modification: Methods Biochem. Anal. 25: 273–301; Bayer and Wilchek (1978): The avidin-biotin complex as a tool in molecular biology: Trends biochem. Sci. 3: N257–259; Bayer et al (1979): Meth. Enzymol. 62: 319–326. Furthermore application of molecular biology could also be possible. By this means, new proteins (fusion proteins) that are based on the genetic information of both the antibiotic binding protein and the enzyme label could be created.

A preferred enzyme label is horse-radish peroxidase, which is known for its stability but also other enzymes can be used. For instance peroxidase, alkaline phosphatase or β-galactosidase in general (all enzymes that are useful in an Enzyme-Linked Immunosorbent Assay, ELISA) (J. W. Goding (1983): Monoclonal antibodies: principles and practice (ISBN 0-12-287020-4). The means of detecting the enzyme will depend on the specific enzyme used. Typically the enzyme label may be detected when the enzyme acts as a catalyst, for example to catalyse a reaction giving rise to a colour change, or when the enzyme inhibits a reaction. Generally, when the presence of the enzyme is detected by means of a colour change, a suitable substrate is added, upon which the enzyme acts. The degree of colour change is then related to the amount of enzyme present. A suitable substrate for a horse-radish peroxidase is for example a chromogenic colour substrate which is easily oxidized by the formation of oxygen such as tetramethylbenzidine, o-phenylenediamine or azinodiethylbenzthiazoline.

Immobilization of the antibiotic of interest may be carried out in a manner known per se, for example by covalent or non-covalent adsorption (P. Tijsen, Practice and Theory of Enzyme Immunoassays, Elsevier, 1985) to a solid matrix (e.g. plate, tube, dipstick or beads (Fe, latex, etc.)). An antibiotic having a lactam-ring can be covalently conjugated to a carrier, optionally via a spacer. All methods available to construct chemical bonds could be suitably used, unless they are detrimental to the antibiotic.

It will be obvious that many coupling techniques can be applied, for instance those known from peptide chemistry and that many bifunctional compounds are suitable as a spacer.

Suitable procedures for instance are the methods described by H. R. Yocum et al. (J. Biol. Chem. (1980), 255, 3977–3986), in which spacers of the general form $X(CH_2)_n$—COOH are used.

A very efficient and reliable method for intermolecular conjugation is described by J. Carlsson et al. (1978) in Biochem. J. 173, 723–737), in which the heterobifunctional reagent N-succinimidyl-3-(2-pyridylthio)-propionate (SPDP) is used.

Materials such as glass or plastics can be used as matrix material. $NH_2$ groups of the matrix can be used to obtain immobilization. Covalent coupling between materials such as plastics (e.g. polystyrene) and a protein (for example BSA) can also be used to immobilise the antibiotic of interest, see e.g. R. H. Burdon and P. H. van Knippenberg, Laboratory techniques in Biochemistry and Molecular Biology, Elsevier, 1985.

According to a preferred embodiment, the antibiotic is immobilized onto the interior surface of a container such as a test tube, preferably via a linking compound such as BSA.

The present invention also provides a kit for carrying out the detection, which comprises at least one enzyme-labelled antibiotic binding protein and at least one immobilized antibiotic.

All patent applications, patents and other documents mentioned in this application are herein incorporated by reference to the same extent as if each individual application or patent or other document was specifically and individually indicated to be incorporated by reference.

In the following examples preferred embodiments are s described to illustrate the invention. However, it is to be understood that the invention is not limited to the specific embodiments and that a person skilled in the art who is familiar with the methods may use other tests which can be equally used for the purpose of the present invention. These so alterations are included in the scope of the invention.

EXAMPLE 1

Antibiotic residue test.

In this example will be described a method for detecting benzylpenicillin residues as low as 5 ppb in milk.

Extraction of antibiotic binding protein

A grown culture of an antibiotic sensitive microorganism in this example *Bacillus stearothermophilus* (continuous culture art. #108 Porton Products Ltd, UK) was lysed overnight at 4° C. with lysozyme, DNAse and triton X-100 in 0.1M phosphate pH 7.0. The lysate was centrifuged for 30 minutes at approximately 1600×g (4° C.). After centrifugation the supernatant was mixed with an antibiotic affinity gel matrix, for example to prepare a 7-aminocephalosporanic acid (7ACA) affinity gel matrix the following method was used.

0.34 g of 7ACA was mixed with 25 ml 0.1M phosphate pH 7.0 (pH corrected to 7). To this solution was added 100 ml beads affigel 10 ® (BioRad) (washed with 1 l 0.1M phosphate pH 7.0). This was mixed gently for 2 hours at 20° C. The 7ACA-affigel 10 was filtered and sucked off using vacuum. The 7ACA-affigel was then washed again with 0.1M phosphate pH 7.0 and was ready for use.

The 7ACA-affigel and the supernatant of the lysed culture was mixed for 3 hours at 20° C. gently on a shaker. The gel was washed six times with 0.1M phosphate+1M NaCl pH 7.0. For each wash was used 500 ml.

20 ml elution-buffer (0.05M phosphate+0.5M NaCl+0.1% triton X-100+0.8M hydroxylamine pH 7.0) was added to the moist gel cake and mixed for 20 minutes at 20° C. gently on a shaker. The mixture was then centrifuged at 4° C., 6 minutes at approximately 300×g. The supernatant was dialysed in 32 mm tubing (12–14 kD cut-off).

The first dialysis was against 0.05M phosphate+0.5M NaCl pH 7.0 overnight at 4° C., the second up to the fifth dialysis was against 0.1M carbonate pH 9.4 with a change of buffer every 4–6 hours. The lysate was centrifugated 20 minutes at approximately 1000×g at 4° C. and concentrated in an AMICON concentrator (ultra filtration) (model #8200, W. R. Grace and Co.) according to the manufacturer's standard operation procedure (SOP). The purified antibiotic binding protein is now ready for conjugation.

Conjugation of antibiotic binding protein (abp) with an enzyme label

In this example horse-radish peroxidase (HRPO) is used. 1 mg HRPO (suitable for labelling) in 1 ml of distilled water (d.i.-water) and 0.2 ml 0.1M Na-periodate was mixed 20 minutes at 20° C. and dialysed overnight at 4° C. against 0.001M Na-acetate pH 4.4. This dialysate was adjusted to pH 9.0-9.6 by adding 25 μl of 0.1M carbonate. Directly hereafter 1 mg abp (Pierce protein assay) was added into the dialysate. The mixture was gently shaken for 2 hours at room temperature. Thereafter 150 μl of 4 mg Na-borohydride/ml d.i.-water was added to the mixture, this was incubated for 2 hours at 4° C.

The solution was dialysed against PBS (0.01M phosphate+0.9% (m/v) NaCl pH 7.0) with four buffer changes every 4 hours.

After the dialysis was completed, the dialysate was diluted in 10% goat sera (inactivated)+0.03% 4-aminoantipyrine. This is named antibiotic binding protein-enzyme (HRPO) conjugate. The highest dilution which gave a fast colour development with the colour-substrate is used in the test-format. Preserving the diluted conjugate with thiomersal gives a highly stable test-kit reagent which can be stored for at least 6 months at 4° C.

Conjugation of a β-lactam to a protein

In this example the basis structure of the cephalosporins (7 amino-cephalosporanic acid (7ACA)) is used for conjugation to Bovine Serum Albumine (BSA). A spacer between the 7ACA and the BSA is used to obtain the best affinity and specificity for β-lactams.

40 mg of 7ACA was added to 4 ml of 50 mM Hepes (pH 7.5) solution. After dissolving the pH was adjusted to pH 7.0 with 1N NaOH. Hereafter 20 mg BSA and 40 mg Bis(sulfosuccinicmidyl)suberate (spacer) and an extra 2 ml of 50 mM Hepes solution was added. The mixture was gently shaken for 45 minutes at 20° C.

After mixing the solution was dialysed (tubing cut-off 12–14 kD) for 48 hours against PBS with three buffer changes. This dialysate is used for tube coating after dilution.

Coating of β-lactam-spacer-protein conjugate to a solid-phase

Coating of this conjugate to a solid-phase makes it possible to use a convenient separation between bound and unbound abp-conjugate. In this example the following method was used:

0.125 ml dialysate (7ACA-spacer-BSA conjugate) was added to 500 ml carbonate pH 9.6. 0.5 ml of this solution was added to the polystyrene star tubes (NUNC MAXISORB ®). Tubes were covered and incubated overnight at 4° C. After incubation the β-lactam spacer protein conjugate dilution was removed from the tubes and 2 ml 0.05M phosphate+0.5% BSA+2% sucrose+0.1M glycine pH 7.2 was added to each tube. After 1 hour at 20° C. the tubes were emptied and dried for 48 hours at 22°-27° C. with less than 30% humidity. Dried tubes are stable for at least 1 year at 4° C.

Wash-solution

A convenient separation method is washing the solid-phase (tubes) with a solution as described below.

Wash solution for separation of conjugate bound to antibiotics coated on solid-phase (tubes) from conjugate bound to 'sample'-antibiotics is prepared as follows:

| | |
|---|---|
| Mono basic sodium phosphate | 11.7 gram/l |
| Dibasic sodium phosphate | 21.6 gram/l |
| Benzalkonium chloride | 3.57 gram/l |
| Glycerol | 500 ml/l |
| Tween 20 | 12.5 ml/l |
| pH adjusted to 6.5. | |

This solution was made 50×concentrated for stability (1 year) and convenient transportation of the final test kit. For the test a 50×dilution in distilled water (or tap water) is used. Also other low salt and surfactant containing solutions may be possible.

Substrate

For the substrate of HRPO it is possible to use a chromogenic colour substrate which is easily oxidized by the formation of oxygen. In this example is used a commercial product TM-blue ® from TSI (U.S. Pat. No. 5,013,646) which has a good stability (for at least 1 year at 4° C.) and operation. The colour-development can be measured by optical density at 650 nanometer wavelength or after acidification at 450 nanometer.

Stop solution

The use of a stop solution such as 1.5% NaF (or strong acids) is highly stable and gives a better quantitative approach in case a difference in colour development is being measured at a time-base.

Test-performance (sequential assay)

0.2 ml of milk sample and 0,2 ml of a diluted abp-enzyme conjugate was added to an empty reaction ampoule. After incubation for 2 minutes at 64° C. the contents of the tube was transferred to the coated tube. After the second incubation of 2 minutes at 64° C. the contents of the coated tube was dumped into the sink and the tubes were washed three times with 50×diluted wash solution by filling the tubes, dumping the contents into the sink and removing residuals by tapping on absorbent paper. After the wash, 0.5 ml of TM-blue ® colour-substrate was added into the tube. This incubation for 4 minutes at room temperature was stopped by adding 0.5 ml of stop solution (1.5% NaF). The colour development at 650 nm was compared with an antibiotic standard tested along with the sample.

A preserved, freeze-dried antibiotic standard is included in the test kit for convenience (stable for at least 1 year).

With this method milk samples with antibiotic residues as little as 5 ppb benzyl penicillin can easily be detected with a total incubation time of 8 minutes. Results of the test are shown in Table I.

TABLE I

| sample | ppb Pen. G present in sample | Reader units* expressed in % |
|---|---|---|
| 1 | 0 | 100 |
| 2 | 1.25 | 96 |
| 3 | 2 | 69 |
| 4 | 3 | 65 |
| 5 | 4 | 51 |
| 6 | 5 | 47 |
| 7 | 10 | 32 |

*Reader units: measured at 650 nanometer wavelength

This test according to this example is also sensitive for other β-lactams see Table II for examples.

TABLE II

| β-lactam antibiotic | sensitivity ppb |
|---|---|
| Amoxicillin | 5 |
| Ampicillin | 10 |
| Cephapirin | 5 |
| Ceftiofur | 5 |

A competitive assay can be performed by combining the first and second incubation step together. This test format will be somewhat faster by elimination of the incubation time of the second step. However the sensitivity as the sequential assay will be smaller.

EXAMPLE 2

Antibiotic residue test

In this example a method will be described for detecting gentamycin residues as low as 30 ppb in milk.

The gentamycin assay is in general developed with the same basics as the β-lactam-assay. We will therefore give in this example the same outline as the β-lactam assay of Example 1 with description of differences.

Obtaining of antibiotic binding protein

A commercial anti-gentamycin-rabbit antibody is obtained from Biodesign International, Kennebunkport, Me., U.S.A. The anti-gentamycin-rabbit antiserum is absorbed to remove the bovine serum albumin (BSA) carrier antibodies. A solution containing 10 mg/ml sulfosuccinicmidylsuberate-BSA and 2 mg of unreacted BSA is mixed with the raw antiserum in the ratio of 10 to 1. This removes all detectable reactivity with BSA.

Conjugation of antibiotic binding protein with an enzyme label

Absorbed anti-gentamycin antiserum is reacted with horseradish peroxidase labelled *Staphylococcus aureus* protein A to form an antibiotic binding protein enzyme conjugate. An optimal ratio of antibody to protein A is determined by forming the assay with checkerboard titrations of the two components diluted in phosphate buffered saline containing 1% BSA.

Conjugation of gentamycin to a protein

In this example gentamycin is used for conjugation to Bovine Serum Albumin (BSA). A spacer between gentamycin and the BSA is used to obtain the best affinity and specificity. The spacer is the same as used in Example 1.

Coating of gentamycin-spacer-protein conjugate to a solid phase

As described in the β-lactam test, the gentamycin-spacer-protein conjugate is coated to a solid phase.

Wash-solution, substrate, stop-solution

Wash-solution, substrate and stop-solution of gentamycin test is the same as used for the β-lactam test.

Test-performance (sequential assay)

The same test method as described in Example 1 for the β-lactam test can be used for the gentamycin test. However, this test uses all incubations at a temperature of 20° C.

With this test method milk samples with antibiotic residues as little as 30 ppb (can be lowered to 2.5 ppb referred to Table III) can easily be detected with a total incubation time of 8 minutes.

Results of the test are shown in Table III.

TABLE III

| Sample | ppb gentamycine present in sample | reader units* expressed in % |
| --- | --- | --- |
| 1 | 0 | 100 |
| 2 | 2.5 | 55 |
| 3 | 5 | 39 |
| 4 | 10 | 31 |
| 5 | 20 | 23 |
| 6 | 30 | 20 |
| 7 | 36 | 18 |

*reader units: measured at 650 nanometer wavelength

EXAMPLE 3

Preparation of N-pentadecakis[N-(4-carbonyl-3-methylceph-3-em-7-yl)aminocarbonylethyldithioethylcarbonyl]bovine serum albumin (1)

Step A:

Preparation of 7β-(2-Pyridyldithiopropionamido)-3-methyl-3-cephem-4-carboxylic acid (2)

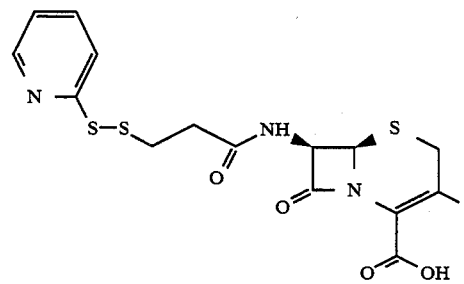

(2)

7β-Amino-3-methyl-3-cephem-4-carboxylic acid (34.28 mg; 0.16 mmol) was suspended in water (7 ml) and, with stirring, pH was brought to 7.1 with 0.1M phosphate buffer, pH 8.0. Then, a solution of N-succinimidyl 3-(2-pyridyldithio)propionate (100 mg; 0.32 mmol) in absolute ethanol (10 ml) was added dropwise while keeping the temperature at about 3° C. The reaction mixture was further stirred for about 72 hours at 3° C., diluted with water (20 ml) and extracted with ether to remove the front moving components. Thereafter, the water-layer was brought to pH 2.5 with 0.1N hydrochloric acid and extracted with ethyl acetate. The combined ethyl acetate extracts were washed with water, dried over anhydrous MgSO₄, solvent removed under reduced pressure and the product (2) dried under vacuum to a constant weight. Yield=28.4 mg.

IR Spectrum (KBr): 3294, 1778, 1712, 1686 cm⁻¹. ¹H NMR (360 MHz; CDCl₃; δ-value in ppm; TMS): 2.06 (3H, CH₃); 2.68, 2.99, [2×m, 2×2H, (CH₂)₂]; 3.24, 3.53, (ABq, $\bar{J}$=18.7 Hz, C²H₂); 5.02 (d, 1H, $\bar{J}$=4.5 Hz, C⁶H); 5.70 (dd, 1H, J=4.5 Hz and J=7.9 Hz, C⁷H); 7.21, 7.77, 7.87, 8.48 (m, 1H; m, 1H; d, 1H; dd, 1H; pyr.); 8.20 (d, 1H, J=7.9 Hz, NH).

Step B:

Introduction of 2-pyridyl disulphide group into bovine serum albumin by N-succinimide 3-(2-pyridylthio)propionate and subsequent thiolation by specific reduction.

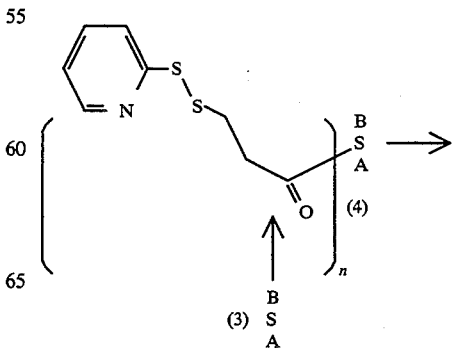

-continued

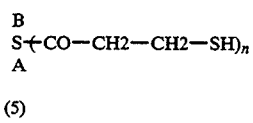

This was performed as described by J. Carlsson, H. Drevin and R. Axén [Biochem. J. (1978) 173, 723].

A solution of N-succinimidyl 3-(2-pyridyldithio)propionate (100 mg; 320 μmol) in absolute ethanol (4 ml) was added dropwise into a stirred solution of bovine serum albumin (BSA) (3) (265 mg; 4.0 μmol) in 0.1M sodium phosphate buffer/0.1M NaCl, pH 7.53 (4 ml) at room temperature (24° C.). After stirring for 35 min at about 24° C., the reaction mixture was separated by gel filtration on Sephadex G-25 (38 g) (elution medium: 0.1M sodium phosphate buffer/0.1M NaCl, pH 7.53). Fractions containing the protein-2-pyridyl disulphide derivative (4) were collected, weight=25.6635 g.

The UV-spectrum measurements of 0.09828 g (4) (from the above combined fractions) after reduction with dithiothreitol (at $\lambda_{max}$ 343 nm) showed that 24 mol of 2-pyridyl disulphide structures/mol of bovine serum albumin have been incorporated.

Thereafter, the combined fractions [containing 4 μmol of bovine serum albumin-2-pyridyldisulphide derivative (4)] were freeze-dried, again dissolved in water (10 ml) and then, with help of gel filtration on Sephadex G-25, the buffer of the concentrated protein-bound-2-pyridyl disulphide derivative (4) was changed to pH 5.81 with 0.1M citric acid-sodium citrate buffer/0.1M NaCl, pH 5.81. The fractions containing bovine serum albumin-2-pyridyl disulphide derivative (4) were combined and treated with dithiothreitol (61.7 mg; 400 μmol) at room temperature (23° C.) and further stirred for 1.5 hours at the same temperature. Then, the protein-bound thiol groups derivative (5) was separated by gel filtration on Sephadex-25 through elution with 0.1M citric acid-sodium citrate buffer/0.1M NaCl, pH 5.81. These fractions were combined and freeze dried.

The buffer pH of the freeze dried product containing bovine serum albumin-bound thiol groups derivative (5) (4 μmol) was transformed to 7.53 by dissolving in 0.1M sodium phosphate buffer/0.1M NaCl, pH 7.53 (5 ml) and then followed by gel filtration over Sephadex-25 using the same buffer as the eluent. The fractions containing the bovine serum albumin derivative (5) were collected, weight=22.8398 g.

Step C:

Reaction of 7β-(2-pyridyldithiopropionamido)-3-methyl-3-cephem-4-carboxylic acid (2) with bovine serum albumin-bound thiol group derivative (5) to form N-pentadecakis[N-(4-carboxyl-3-methylceph-3-em-7-yl)aminocarbonylethyldithioethylcarbonyl]bovine serum albumin (1)

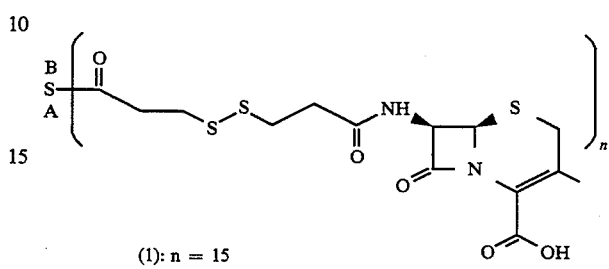

(1): n = 15

A solution of 7β-(2-pyridyldithiopropionamido)-3-methyl-3-cephem-4-carboxylic acid (2) (34.28 mg) from Step A in 0.1M sodium phosphate buffer/0.1M NaCl, pH 7.53 was added to a stirred solution of bovine serum albumin-bound thiol groups derivative (5) from Step B (9.1433 g; 1.6 μmol) at 20° C. The reaction mixture was further stirred for 2 hours at 20° C. and left for two days at 0° C. The UV-spectrum measurements of the reaction mixture (at $\lambda_{max}$ 343 mm) showed that 15 mol of N-(4-carboxyl-3-methylceph-3-em-7yl)aminocarbonylethyldithioethylcarbonyl units (n=0)/mol of bovine serum albumin have been introduced. Thereafter, the reaction mixture was purified by gel filtration on Sephadex G-25 (elution medium: 0.1M sodium phosphate buffer/0.1M NaCl, pH 7.53). The fractions having $\lambda_{max}$ 265 nm were collected and freeze dried.

The freeze dried product was unsalted with help of gel filtration on Sephadex G-25 using water as the eluent. The fractions containing N-pentadecakis[N-(4-carboxy-3-methylceph-3-em-7-yl)aminocarbonylethyldithioethylcarbonyl]bovine serum albumin (1) were combined and freeze dried.

Yield=93.6 mg. The product (1) has been identified through $^1$H NMR spectrum (600 MHz; D$_2$O; δ-value) showing β-lactam protons at 5.60 and 4.98 ppm respectively and a C$\underline{H}_3$ signal at 1.92 ppm.

I claim:
1. A process for the detection of a β-lactam in a liquid medium consisting essentially of
   (a) bringing together a fluid sample of the liquid medium, a labelled β-lactam binding protein obtained from a *Bacillus stearothermophilus* and immobilized 7-amino-cephalosporanic acid conjugated to Bovine Serum Albumin (BSA),
   (b) allowing the labelled antibiotic binding protein to bind with the immobilized 7-amino-cephalosporanic acid,
   (c) removing labelled antibiotic binding protein which is not bound to the immobilized antibiotic, and
   (d) detecting the β-lactam by determining the amount of the labelled antibiotic binding protein bound to the immobilized 7-amino-cephalosporanic acid which is inversely related to the β-lactam in the liquid medium.
2. A process according to claim 1 wherein the liquid medium is milk, urine or blood.

3. A process according to claim 1 wherein step (a) comprises bringing the labelled antibiotic binding protein into contact with the liquid sample, allowing the antibiotic in the sample to bind to the labelled antibiotic binding protein, and subsequently adding immobilized antibiotic.

4. A process according to claim 1 wherein the immobilized antibiotic is identical to that present in the liquid sample.

5. A process according to claim 1 wherein the immobilized antibiotic is different from that present in the liquid sample.

6. A process according to claim 1 wherein the label is an enzyme.

7. A process according to claim 1 wherein the label is a fluorescent compound.

8. A process according to claim 1 wherein the β-lactam binding protein is obtained by affinity chromatography.

9. A process of claim 6 wherein the label is a peroxidase.

10. A process of claim 9 wherein the label is horseradish peroxidase.

11. A kit for the process of claim 1 comprising at least one labelled β-lactam binding protein obtained from a *Bacillus stearothermophilus* and immobilized 7-aminocephalosporanic acid conjugated to bovine serum albumin.

* * * * *